(12) United States Patent
Mlambo et al.

(10) Patent No.: US 10,571,372 B2
(45) Date of Patent: Feb. 25, 2020

(54) METHOD AND APPARATUS FOR FILTRATION OF SAMPLES FOR ONLINE ANALYZERS

(71) Applicant: Ecolab USA Inc., St. Paul, MN (US)

(72) Inventors: Darlington Mlambo, Naperville, IL (US); David R. Szymborski, Oswego, IL (US); David P. Workman, Naperville, IL (US); Michael J. Murcia, DeKalb, IL (US)

(73) Assignee: ECOLAB USA INC., St. Paul, MN (US)

( * ) Notice: Subject to any disclaimer, the term of this patent is extended or adjusted under 35 U.S.C. 154(b) by 187 days.

(21) Appl. No.: 15/146,206

(22) Filed: May 4, 2016

(65) Prior Publication Data
US 2016/0327459 A1 Nov. 10, 2016

Related U.S. Application Data

(60) Provisional application No. 62/157,592, filed on May 6, 2015.

(51) Int. Cl.
*G01N 1/34* (2006.01)
*G01N 1/10* (2006.01)
(Continued)

(52) U.S. Cl.
CPC ............... *G01N 1/34* (2013.01); *C02F 1/001* (2013.01); *C02F 1/004* (2013.01); *G01N 1/10* (2013.01);
(Continued)

(58) Field of Classification Search
CPC .......... G01N 1/34; G01N 1/2035; G01N 1/10; G01N 2001/205; C02F 1/004;
(Continued)

(56) References Cited

U.S. PATENT DOCUMENTS 4,021,339 A 5/1977 Foody
4,294,124 A * 10/1981 Kalwaitis ................. G01N 1/10
73/863.85

(Continued)

FOREIGN PATENT DOCUMENTS

| JP | H 06304584 A | 11/1994 |
| JP | H 0735275 A | 2/1995 |
| JP | H 09189071 A | 7/1997 |

OTHER PUBLICATIONS

"RF 600R Range of Filters Technical Specifications," Rotortlush Filters Ltd. (Charmouth, Dorset, UK) brochure, publication date unknown, 4 pages.
(Continued)

*Primary Examiner* — Liam Royce
(74) *Attorney, Agent, or Firm* — Eric D. Babych; Barnes & Thornburg LLP

(57) ABSTRACT

A filtration apparatus and methods of installing, using, and retracting the same. A filtration apparatus includes a compression gland, a ball valve, and a filter pipe. A distal portion of the filter pipe has one or more filtration holes. The filtration apparatus may be installed in a process pipe and the distal portion of the filter pipe may be disposed within the process pipe. The filter pipe can be easily retracted from the process pipe without interruption of the industrial process. The filtration apparatus can be automatically cleaned by compressed air or water.

8 Claims, 3 Drawing Sheets

(51) Int. Cl.
*C02F 1/00* (2006.01)
*G01N 1/20* (2006.01)
*C02F 103/32* (2006.01)
*C02F 103/28* (2006.01)
*C02F 103/22* (2006.01)

(52) U.S. Cl.
CPC ...... *C02F 2103/22* (2013.01); *C02F 2103/28* (2013.01); *C02F 2103/32* (2013.01); *C02F 2209/02* (2013.01); *C02F 2209/06* (2013.01); *C02F 2209/11* (2013.01); *G01N 1/2035* (2013.01); *G01N 2001/205* (2013.01)

(58) Field of Classification Search
CPC .. C02F 1/001; C02F 2209/11; C02F 2209/02; C02F 2209/06; C02F 2103/28; C02F 2103/32; B01D 35/02; B01D 35/04
USPC .......................................................... 210/174
See application file for complete search history.

(56) References Cited

U.S. PATENT DOCUMENTS

| | | | |
|---|---|---|---|
| 4,707,257 A | 11/1987 | Davis et al. | |
| 5,134,879 A * | 8/1992 | Wong | E21B 49/086 |
| | | | 73/61.72 |
| 5,186,324 A * | 2/1993 | Brandon, Jr. | B60P 1/162 |
| | | | 137/592 |
| 5,641,894 A * | 6/1997 | Hosokawa | G01N 1/2035 |
| | | | 73/64.56 |
| 5,972,211 A | 10/1999 | Jones | |
| 6,379,621 B1 * | 4/2002 | Schwab | G01N 1/14 |
| | | | 210/321.69 |
| 6,675,664 B1 * | 1/2004 | Lilienthal | G01N 1/2035 |
| | | | 210/122 |
| 8,998,172 B2 * | 4/2015 | Lewandowski | F16K 5/0673 |
| | | | 251/188 |
| 2008/0288111 A1 * | 11/2008 | Yamaguchi | C02F 1/5209 |
| | | | 700/271 |
| 2012/0141100 A1 * | 6/2012 | Evans | F24H 1/142 |
| | | | 392/485 |
| 2015/0196046 A1 * | 7/2015 | Lee | C02F 11/14 |
| | | | 426/601 |

OTHER PUBLICATIONS

"Rotorflush Filter System for Fluid Analysers," Rotortlush Filters Ltd. (Charmouth, Dorset, UK) brochure, publication date unknown, 1 page.

International Search Report and Written Opinion from related PCT App. No. PCT/US2016/030641, dated Aug. 11, 2016, (10 pages).

* cited by examiner

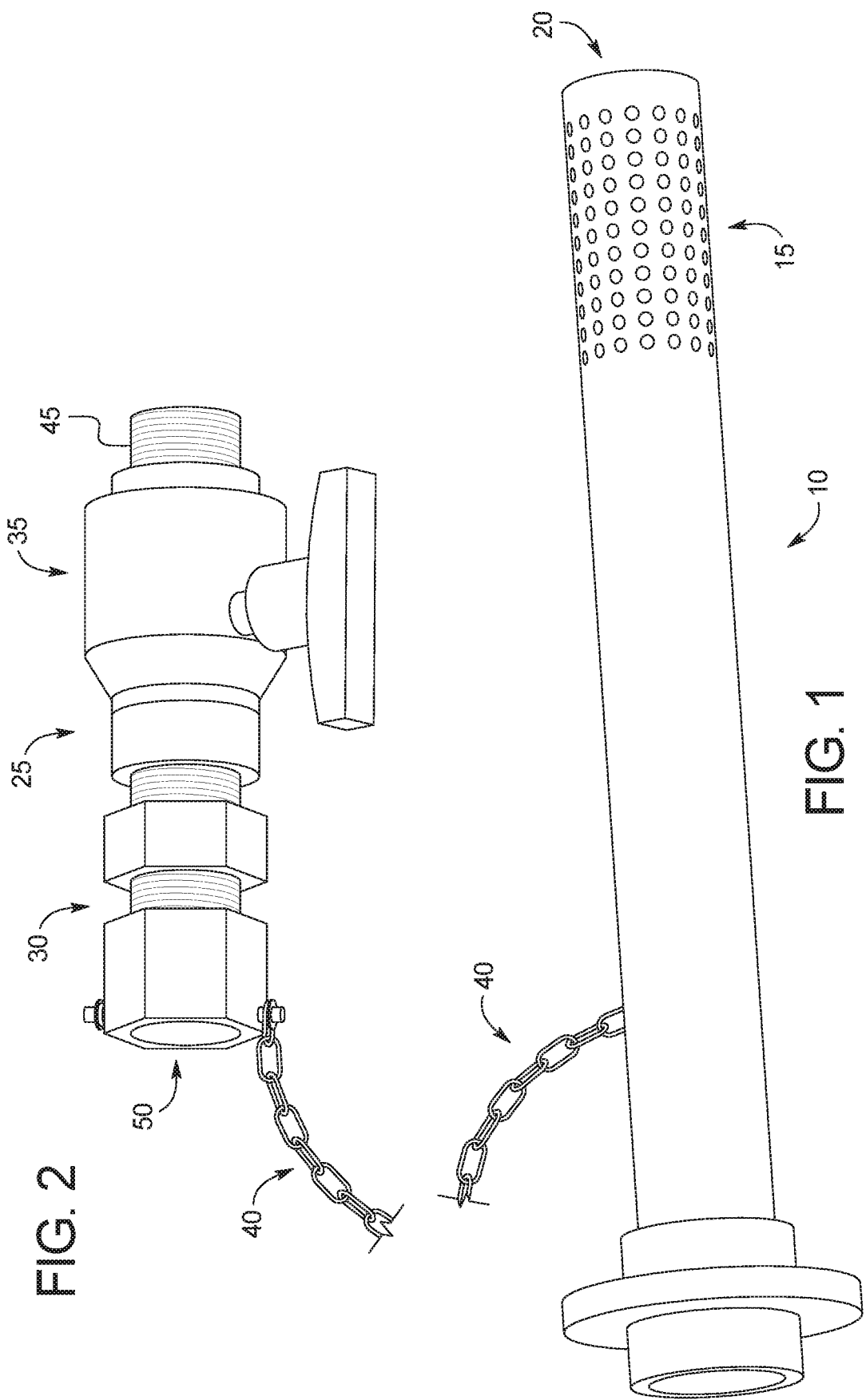

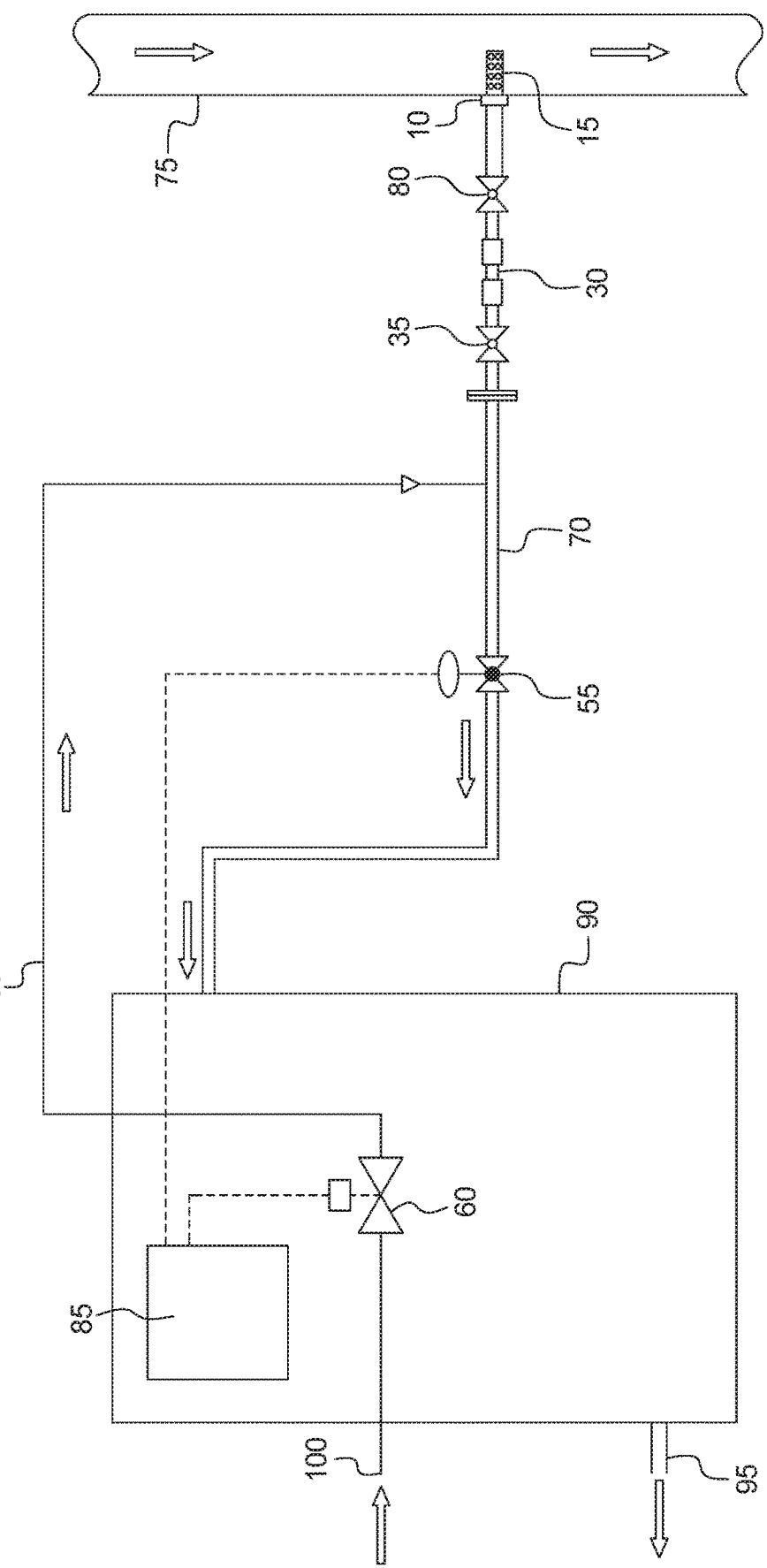

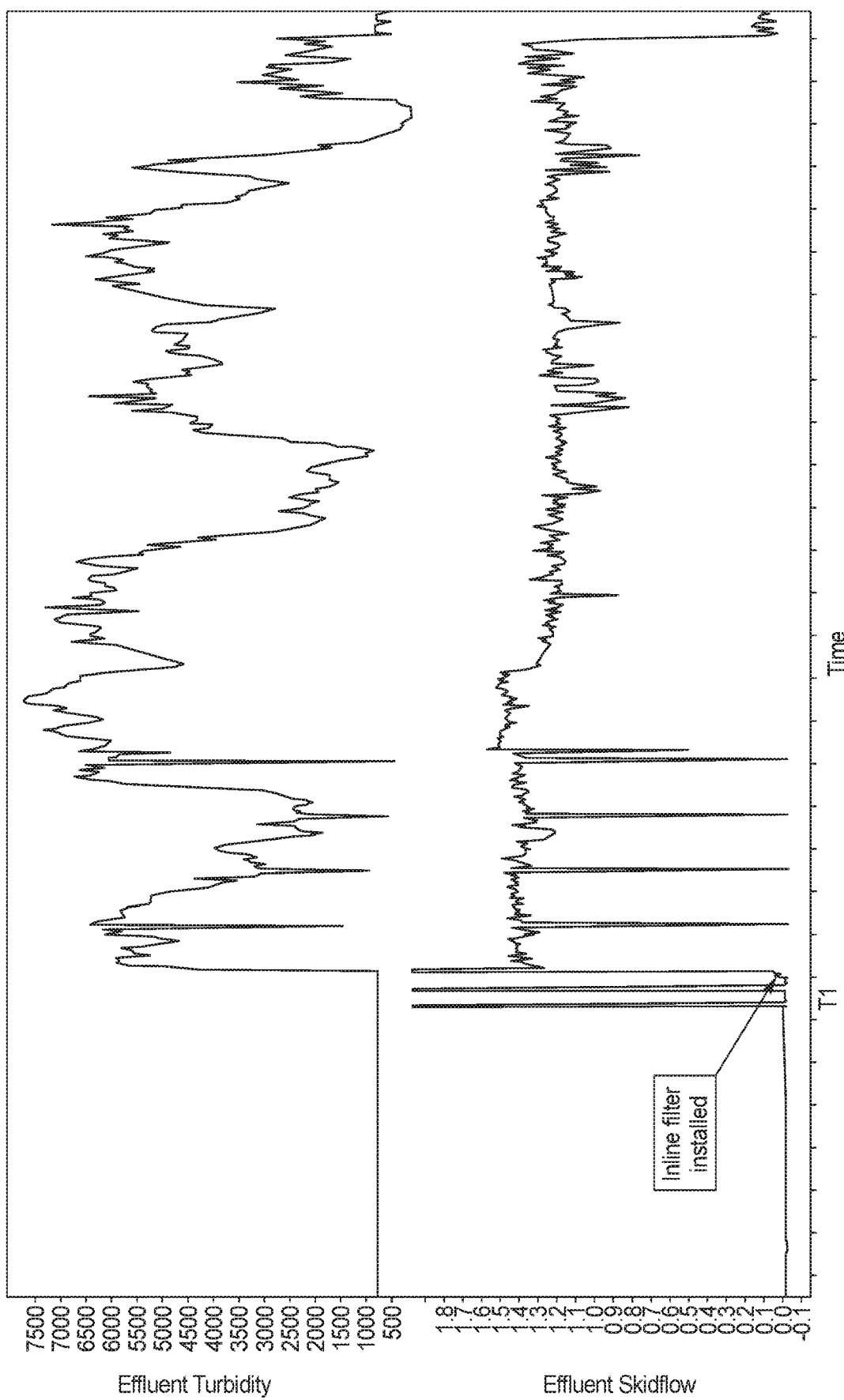

METHOD AND APPARATUS FOR FILTRATION OF SAMPLES FOR ONLINE ANALYZERS

BACKGROUND

1. Field of the Invention

The present disclosure generally relates to filtration devices. More particularly, the present disclosure concerns filtration devices that may be used in industrial processes and methods for installing, retracting, and cleaning such filtration devices.

2. Description of the Related Art

Industrial water systems commonly include components such as sample pumps and analyzers. The water of these systems generally needs to be monitored and controlled to avoid problems associated with, for example, scaling and microbiological growth. Sample pumps may be used to transport water from the system to one or more analysis devices where the water is analyzed to determine if any remedial action needs to be taken. Some systems include strainers to filter the water before it enters the sample pumps and/or analysis devices.

Some industrial systems use basket strainers for water filtration purposes. However, the strainers known in the art are susceptible to plugging and/or clogging. While self-cleaning strainers may be available generally, these types of strainers are not capable of being used in process water pipes. Moreover, their self-cleaning mechanism requires the use of large amounts of water or sample flow, which is not sustainable in applications such as sampling for the purposes of analyzing a primary wastewater treatment plant effluent stream. As such, a self-cleaning strainer is needed for installation in process pipes of industrial water systems.

BRIEF SUMMARY

The present disclosure relates to a filtration apparatus and methods of installing, using, and retracting the same. In one embodiment, a method of filtering debris from a liquid in an industrial process is disclosed. The method comprises the steps of providing a process pipe comprising a liquid and attaching a distal end of a ball valve to an opening in a wall of the process pipe, a proximal end of the ball valve being attached to a distal end of a compression gland. A filter pipe is slidably disposed within a channel running through the ball valve and the compression gland such that a distal portion of the filter pipe protrudes from the distal end of the ball valve into the process pipe and a proximal end of the filter pipe protrudes from a proximal end of the compression gland. The proximal end of the filter pipe is attached to a distal end of a conduit, a distal end of the filter pipe comprises a cap, and the distal portion of the filter pipe comprises one or more filter holes. The liquid is allowed to flow from the process pipe, through the filter pipe, and into the conduit, wherein the one or more filter holes prevent passage of debris contained in the liquid into the filter pipe.

In another embodiment, a filtration apparatus is disclosed. The filtration apparatus comprises a compression gland having a proximal end, a distal end, and a channel therethrough, the distal end of the compression gland being attached to a proximal end of a ball valve. The apparatus additionally comprises a filter pipe disposed within the compression gland and the ball valve, the filter pipe having a proximal end, a distal portion, and a distal end, the distal end comprising a cap and the distal portion comprising one or more filter holes. The distal portion of the filter pipe protrudes from a distal end of the ball valve and the proximal end of the filter pipe protrudes from the proximal end of the compression gland.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which:

FIG. 1 shows a filter pipe;

FIG. 2 shows a retraction assembly;

FIG. 3 shows various components that may be involved in a method of filtering process water and a method of cleaning and retracting a filtration apparatus; and FIG. 4 depicts data from experiments that were conducted to test an embodiment of the presently disclosed filtration apparatus.

DETAILED DESCRIPTION

Various embodiments are described below with reference to the drawings. The relationship and functioning of the various elements of the embodiments may better be understood by reference to the following detailed description. However, embodiments are not limited to those illustrated in the drawings or explicitly described below. It should be understood that the drawings are not necessarily to scale, and in certain instances details may have been omitted that are not necessary for an understanding of embodiments disclosed herein, such as conventional fabrication and assembly.

In the present application, the terms "proximal" and "distal" are used to describe the opposing axial ends of particular components of the filtration apparatus disclosed herein. In some embodiments, the filtration apparatus is installed in between a process pipe and a side stream pipe. The term "proximal" is used in its conventional sense to refer to the end of an apparatus (or component thereof, such as a filter pipe) that is closest to the side stream pipe or furthest from the process pipe. The term "distal" is used in its conventional sense to refer to the end of the apparatus (or component thereof, such as the filter pipe) that is closest to the process pipe.

The present disclosure relates to a filtration apparatus that may be used in, for example, process pipes of industrial systems. In some embodiments, the filtration apparatus may be used in connection with the analysis of a primary wastewater treatment plant effluent stream. Sample pumps and/or analyzers are generally utilized to analyze the effluent. The filtration apparatus acts as a strainer to prevent debris from flowing into the sample pumps and analyzers. In accordance with the present disclosure, it is to be understood that "debris" means any object or composition of matter that may be contained in the liquid being passed through the filter. For example, if the stream being filtered was used in paper manufacturing, the debris may be pulp.

In particular embodiments, the filtration apparatus may be used in connection with a system where a side stream is taken from the industrial process pipe. The side stream is used to transport liquid from the system to an online analyzer and the filtration apparatus may be inserted into the system between the process pipe and the side stream pipe to filter out any debris that may attempt to enter the side stream pipe. In some embodiments, a filter pipe of the filtration apparatus extends into the process pipe. For example, a sample tap may be drilled into a process pipe and a portion of the filter pipe may be inserted into the process pipe via the drilled tap.

In some embodiments, the presently disclosed filtration apparatus may be used in connection with an online analyzer. The online analyzer is in fluid communication with a liquid in an industrial system and the filtration apparatus may be used to prevent the flow of debris into the analyzer. In some embodiments, a side stream is used to transport liquid from the system to the analyzer and the filtration apparatus may be used to filter the liquid before it enters the side stream pipe or while it flows through the side stream pipe.

In some embodiments, the filtration apparatus is self-cleaning, meaning that any debris which might cause clogging or plugging may be automatically purged from the filtration apparatus before the apparatus becomes plugged or clogged or when the apparatus becomes plugged or clogged. In some embodiments, a portion of the filtration apparatus is disposed inside of a process pipe. In certain embodiments, the filtration apparatus is an in-line strainer that can be inserted into and retracted from a process pipe, or retracted from any location where it may be installed, if maintenance is needed.

As can be seen in FIG. 1, in some embodiments, the filtration apparatus comprises a filter pipe (10) comprising, for example, stainless steel or polyvinyl chloride (PVC). The diameter of the filter pipe (10) may be chosen by one of skill in the art depending upon the desired application of the filtration apparatus. In some embodiments, the diameter of the filter pipe may be about 0.5 inches to about 2 inches. The diameter of the filter pipe (10) may vary along the length of the pipe in some embodiments. The length of the filter pipe (10) can also be chosen by one of skill in the art depending on the desired application of the filtration apparatus. In some embodiments, the length of the filter pipe may be about 5 inches to about 20 inches or more.

For example, compressed air or water may be injected into the filter pipe to back flush/unplug/clean the pores/holes (15) near the distal end of the pipe. If the filter pipe (10) has a length ranging from about 1 inch to about 20 inches, the injected air or water will have sufficient force to clean/unplug all filtration holes (15) near the distal end of the pipe. As the pipe gets longer than 20 inches, for example, the force of air or water will weaken as it travels to the distal end of the filtration pipe and cleaning of the holes (15) may not be as efficient.

A distal portion of the filter pipe (10), which comprises the filtration holes (15), may be inserted into a process pipe to filter a liquid flowing through the process pipe and into an analyzer. The distal end (20) of the filter pipe includes a plug (not shown) which blocks liquid flow into the distal end of the filter pipe. As noted above, the distal portion of the filter pipe (10) comprises one or more filter holes (15) that allow a sufficient volume throughput of liquid to flow into the filter pipe (10) but block larger debris from flowing into the filter pipe (10). While the filter holes (15) are shown at a distal portion of the filter pipe (10), some embodiments of this disclosure may include filtration holes (15) near the mid-section of the filter pipe (10) provided that the holes are contained within the process pipe.

The diameter of the filter holes (15) can be chosen by one of ordinary skill in the art depending on the size of debris in the liquid that needs to be filtered. In some embodiments, the filter holes (15) may comprise a diameter of about 1/16 inch to about 1/2 inch. In certain embodiments, the diameter of the filter holes (15) may be about 3/16 inch or about 1/4 inch. The filter holes should provide sufficient volume throughput for the sample volume to be enough to flow to the analyzer.

In accordance with FIG. 2, the filtration pipe may comprise a retraction assembly (25). The retraction assembly (25) may comprise a compression gland (30) and a ball valve (35). A distal end of compression gland (30) may be attached to a proximal end of ball valve (35) using any suitable means that can form an air-tight and/or liquid-tight seal, such as using threads, adhesives, soldering, welding, and the like. A distal end of filter pipe (10) passes through a channel in the compression gland (30) and the ball valve (35), when the ball valve is in its open position, and protrudes from a distal ball valve end. The retraction assembly (25) allows a distal portion of filter pipe (10) to be inserted into, and pulled out of, a process pipe without having to shut down the entire industrial system.

In some embodiments, a distal end of the ball valve (35) comprises threads (45) on its outer surface and the hole drilled in the process pipe comprises complementary threads that engage with the threads on the distal end of ball valve (35). As such, a distal end of ball valve (35) may be threaded into a hole in the process pipe, thereby forming an air-tight and/or liquid-tight seal. Since the filter pipe (10) extends past the distal end of ball valve (35), when the distal end of ball valve (35) is secured to the process pipe, a distal portion of filter pipe (10) will be within the process pipe. In some embodiments, the distal end of filter pipe (10) extends into the process pipe a distance of more than about 1/4 of the process pipe diameter, such as a distance of about 1/3 or about 1/2 of the process pipe diameter. Although threads have been described as a means to join the process pipe and the ball valve, any other method may be used to join these components, such as adhesives, welding, and the like.

The compression gland (30) functions to prevent leaks. In some embodiments, the compression gland (30) may be rated to withhold pressure up to about 100 psi at 75 psi. Any commercially available compression gland may be used in connection with the presently disclosed filtration apparatus. The compression gland (30) may be loosened, thereby allowing the filter pipe to slide therethrough. Upon loosening the compression gland, the distal end of the filter pipe may be slid through the compression gland, through the ball valve, and into the process pipe. Once the distal end of the filter pipe is at the desired location in the process pipe, the compression gland may be tightened, thereby holding the filter pipe in place and preventing any further movement thereof.

The proximal end of filter pipe (10) protrudes from the proximal end (50) of the compression gland (30) and may be attached to a side stream pipe, or any other conduit that may be used to transport liquid to an analyzer, using threads, welding, or any other attachment means. The point of attachment forms an air-tight and/or liquid-tight seal. In some embodiments, the proximal end of the compression gland (30) comprises a safety chain (40) connected to the proximal end of filter pipe (10) in case there is pressure built up in the pipe.

Other aspects of the present disclosure relate to an automated method of cleaning the filtration apparatus. In some embodiments, the method comprises automatically injecting compressed air or water into the filter pipe to back flush the filtration apparatus. In certain embodiments, such as shown in FIG. 3, the cleaning system comprises a pneumatic ball valve (55) that, when closed, directs injected air or water to the filter pipe (10). The cleaning system may also comprise an air injection (or water injection) solenoid valve (60). An electrical signal may be sent to the solenoid valve (60) to open the valve to allow the flow or compressed air or water. An electrical signal may also be sent to close ball valve (55). In the present disclosure, electrical signals may be sent by a controller. A conduit (65) transports the air or water to a side stream pipe (70). Once the air or water enters the side stream pipe (70), it travels distally (since ball valve (55) is closed), to the filter pipe (10). The force behind the compressed air or water causes the air or water to exit through the filter holes (15), thereby causing any debris that has accumulated around the filter holes (15) to become dislodged. Once the debris is dislodged, it flows downstream through the process pipe (75) and goes, for example, to waste.

In connection with the system depicted in FIG. 3, it can be seen that a distal portion of the filter pipe (10) may be inserted into the process pipe (75) such that the longitudinal axis of the process pipe (75) and the longitudinal axis of the filter pipe (10) are perpendicular or substantially perpendicular. Wastewater or some other liquid flows through the process pipe (75) in the direction shown and a portion of that liquid may be diverted to a side stream pipe (70). Before it enters the side stream pipe (70), the liquid passes through the holes (15) near the distal end of the filter pipe (10), thereby blocking any debris larger than the diameter of the filter holes (15) from entering the side stream pipe (70).

Once the liquid enters the side stream pipe (70), it is directed through ball valve (55) to an inlet of an analyzer (85). In some embodiments, the analyzer (85) is provided on a skid (90), which allows the analyzer to be mobile. The skid (90) may comprise an inlet for transportation of the liquid to the analyzer (85). Once the liquid enters the analyzer (85), various properties of the liquid may be measured, such as, but not limited to, pH, temperature, turbidity. After the liquid analysis has been completed, the liquid may be discarded through an analyzer outlet or a skid outlet (95).

After a certain period of time, which may be from a few hours or days to a few months, depending upon the amount and size of debris in the process waters, the filter pipe (10) may need to be cleaned or unplugged. As noted above, cleaning may be automatically accomplished by sending an electrical signal to a compressed air or water supply pump (100). Automatic cleaning frequency can be programmed or loss of flow to the analyzer can be used as a signal to indicate that the filter pipe needs to be cleaned. An electrical signal is also sent to solenoid valve (60), causing it to open and allow flow of the air or water through conduit (65) and into side stream pipe (70). An electrical signal may also be sent to ball valve (55) causing it to close. Once inside of side stream pipe (70), the air or water flows through retraction assembly (25) and into filter pipe (10). The air or water exits through the holes (15) in filter pipe (10), thereby dislodging any debris that has accumulated at or near filter holes (15).

The air or water may flow through filter pipe (10) for a predetermined amount of time, which may be set by an operator of the system, until all debris has been dislodged and all holes (15) have been cleared. Once the holes (15) are cleared of debris, an electric signal may be sent to the compressed air or water supply pump (100) to stop injection. An electric signal may also be sent to solenoid valve (60) to close the valve and an electrical signal may be sent to ball valve (55) causing it to open. The process system may then return to normal operation where liquid from the process stream enters into filter pipe (10) and travels to the analyzer (85) for analysis.

If, for any reason, the filter pipe needs to be disconnected from the industrial process pipe, this can be easily accomplished by using the retraction assembly (25) and the industrial process does not need to be shut down or disturbed. As described above, in some embodiments, compression gland (30) may be loosened such that filter pipe (10) can be proximally withdrawn such that its distal end passes through the ball valve (80), through the compression gland (30), and out of the proximal end of the compression gland. Once the distal end of filter pipe (10) has passed through ball valve (35), ball valve (35) may be closed to prevent any process liquid from flowing out of the process pipe (75).

In one embodiment, the filtration apparatus may be in fluid communication with a wastewater stream of a meat plant. The filtration apparatus allows the wastewater stream to be analyzed so that the treatment process and recovery of oil, grease, and protein content can be optimized. However, the presently disclosed filtration apparatus may be installed in any industrial process where filtration of a liquid may be advantageous and also where a self-cleaning filter may be advantageous. Some industrial processes may include food and beverage systems and pulp and paper systems. Mining processes are also applicable where the filtration apparatus may be installed in connection with the analysis of effluent from thickeners, for example. The filtration apparatus may be used in connection with any system where online sensors or analysis devices need to be protected from debris that are not required for accurate detection of the process liquid being analyzed.

In connection with the filtration apparatus, an automated platform may be developed. For example, an automated platform may be developed to automatically control wastewater treatment chemicals in a dissolved air flotation (DAF) unit through real time monitoring of certain characteristics of the effluent. Illustrative, non-limiting characteristics of the effluent that may be monitored include, for example, turbidity, pH, and temperature.

In accordance with all embodiments disclosed in the present application, injection of certain chemicals, such as coagulants, flocculants, oxidizing agents, biocides, acids, bases, etc., to remedy certain undesired characteristics of the process water may be carried out using manual injection or automated injection.

For example, the pH of a wastewater stream may be monitored by the presently disclosed analyzer. If the pH of the stream is lower than desired, then a base may be added to the wastewater stream to raise the pH. In certain aspects, the system may include a monitoring and controlling unit that comprises a controller device and a plurality of sensors. Each of the plurality of sensors may be configured to obtain a different characteristic of the analyzed fluid and each sensor may be in communication with the controller. For example, the system may comprise a sensor that measures turbidity, a sensor that measures pH, and/or a sensor that measures temperature. The system may include one or more additional sensors to measure or monitor any other characteristics of the system fluid, such as oxidation-reduction potential.

Based on signals received from the sensors, the controller may send signals to the one or more chemical injection pumps, which are in fluid communication with various chemicals, such as coagulants, flocculants, acids, bases, etc. The signals may turn the pumps off (cause them to stop adding chemical) or turn the pumps on (cause them to add a specified amount of more chemical). The components of this automated system may be in communication with each other in any number of ways, including, as illustrative examples, through any combination of wired connection, a wireless connection, electronically, cellularly, through infrared, satellite, or according to any other types of communication networks, topologies, protocols, and standards.

As used herein, the term "controller" or "controller device" refers to a manual operator or an electronic device having components such as a processor, memory device, digital storage medium, a communication interface including communication circuitry operable to support communications across any number of communication protocols and/or networks, a user interface (e.g., a graphical user interface that may include cathode ray tube, liquid crystal display, plasma display, touch screen, or other monitor), and/or other components. The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, internet connection, microwave link, infrared link, wired network (e.g., Ethernet) and the like. In addition, other components such as a signal conditioner or system monitor may be included to facilitate signal transmission and signal-processing algorithms.

EXAMPLES

In accordance with the configuration depicted in FIG. 3, a filtration and analysis system was set up in the field at a meat processing plant. Before the in-line filtration apparatus was installed, the skid was unable to get sample flow due to plugging of one or more sample pumps that are used to pump sample water into the analyzer. After the in-line filtration apparatus was installed, sample flowed to the skip, allowing for reliable online effluent turbidity measurements, as can be seen in FIG. 4. The bottom graph in FIG. 4 shows that sample flow to the skid was blocked until about time period 1 (T1), which is the time when the filtration apparatus was installed. As can be seen from the graph, after T1, when the filtration apparatus was installed, sample flow was able to reach the analyzer. The top graph in FIG. 4 shows that no turbidity measurements were able to be taken until T1 (when the filtration apparatus was installed), and thereafter, sample turbidity measurements were able to be taken by the analyzer.

To further test the filtration apparatus, a laboratory test was conducted in accordance with the configuration shown in FIG. 3 using a pulp sample from the pulp and paper industry. Over a period of time, the holes in the filter pipe became plugged by pulp in the process water. The automated cleaning method was carried out and it was confirmed that the cleaning method was successful in dislodging all pulp debris that clogged the filter holes in the filter pipe.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of filtering debris from a liquid in an industrial process comprising:
   attaching a distal end of a ball valve to an opening in a wall of a process pipe comprising a liquid, a proximal end of the ball valve being attached to a distal end of a compression gland, wherein a filter pipe is slidably disposed within a channel running through the ball valve and the compression gland such that a distal portion of the filter pipe protrudes from the distal end of the ball valve into the process pipe and a proximal end of the filter pipe protrudes from a proximal end of the compression gland, the proximal end of the filter pipe being attached to a distal end of a conduit, a distal end of the filter pipe comprising a cap, and the distal portion of the filter pipe comprising one or more filter holes;
   allowing the liquid to flow from the process pipe, through the filter pipe, and into the conduit, wherein the one or more filter holes prevent passage of debris contained in the liquid into the filter pipe, wherein a proximal end of the conduit is attached to an analyzer and the liquid flows through the conduit and into the analyzer to analyze one or more properties of the liquid selected from the group consisting of pH, temperature, and turbidity,
   and
   injecting a coagulant into the process pipe, wherein the liquid is a wastewater stream of a meat plant.

2. The method of claim 1, wherein the one or more filter holes comprise diameters of about 1/16 inch to about 1/2 inch.

3. The method of claim 1, wherein the distal portion of the filter pipe extends into the process pipe a distance of about ¼ of a diameter of the process pipe to about ½ of the diameter of the process pipe.

4. The method of claim 1, wherein a diameter of the filter pipe is about 0.5 inches to about 2 inches.

5. The method of claim 1, wherein a length of the filter pipe is from about 5 inches to about 20 inches.

6. The method of claim 1, further comprising the steps of:
loosening the compression gland;
   proximally withdrawing the filter pipe such that its distal end passes through the ball valve, through the compression gland, and out of the proximal end of the compression gland;
   wherein once the distal end of the filter pipe passes through the ball valve, the ball valve is closed to prevent liquid from flowing out of the opening in the wall of the process pipe.

7. The method of claim 1, further comprising the steps of:
closing a valve disposed in the conduit to prevent the liquid from flowing from the conduit into an analyzer;
   opening a solenoid valve to allow compressed air or water to flow into the conduit at a position distally located from the valve disposed in the conduit; and
   allowing the air or water to travel distally through the conduit and into the filter pipe, wherein the air or water flows out of the one or more filter holes in the filter pipe, thereby dislodging any debris contacting the one or more filter holes.

8. The method of claim 1, wherein the process pipe, the filter pipe and the conduit are in fluid communication while the liquid flows from the process pipe into the conduit.

\* \* \* \* \*

UNITED STATES PATENT AND TRADEMARK OFFICE
CERTIFICATE OF CORRECTION

PATENT NO. : 10,571,372 B2  
APPLICATION NO. : 15/146206  
DATED : February 25, 2020  
INVENTOR(S) : Darlington Mlambo et al.

It is certified that error appears in the above-identified patent and that said Letters Patent is hereby corrected as shown below:

On the Title Page

In Column 2, item (56), under Other Publications, Line 1, please replace "Rotortlush" with --Rotorflush--.

Signed and Sealed this  
Thirtieth Day of June, 2020

Andrei Iancu  
*Director of the United States Patent and Trademark Office*